Figure 1:
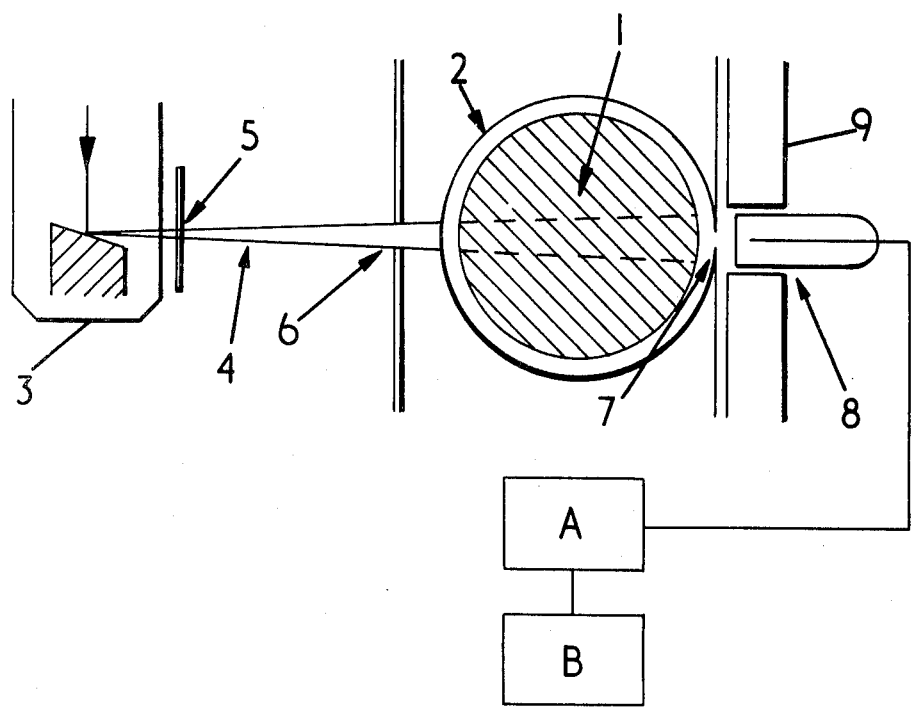

United States Patent [19]

Jury et al.

[11] 4,429,410
[45] Jan. 31, 1984

[54] APPARATUS AND METHOD FOR ASSESSING THE CONCENTRATION OF MINERAL MATTER IN COAL-DERIVED LIQUIDS

[75] Inventors: Anthony W. Jury, Beckford; Geoffrey J. Pitt, Cheltenham, both of England

[73] Assignee: Coal Industry (Patents) Limited, London, England

[21] Appl. No.: 229,470

[22] Filed: Jan. 29, 1981

[30] Foreign Application Priority Data

Feb. 15, 1980 [GB] United Kingdom ............... 805239

[51] Int. Cl.$^3$ ............................................. G01N 23/06
[52] U.S. Cl. .......................................... 378/53; 378/88
[58] Field of Search ................... 250/358 R, 395, 393

[56] References Cited

U.S. PATENT DOCUMENTS 3,200,247  8/1965  Sahores ........................ 250/358 R
3,210,541 10/1965  Cropper et al. ............... 250/358 R
3,270,200  8/1966  Rhodes ......................... 250/358 R

FOREIGN PATENT DOCUMENTS 762432  11/1956  United Kingdom .
983971   2/1965  United Kingdom .
1017595  1/1966  United Kingdom .
1094621 12/1967  United Kingdom .
1427295  3/1976  United Kingdom .
1432826  4/1976  United Kingdom .

Primary Examiner—Alfred E. Smith
Assistant Examiner—T. N. Grigsby
Attorney, Agent, or Firm—Stevens, Davis, Miller & Mosher

[57] ABSTRACT

Mineral matter is coal-derived liquids such as coal extracts can be assessed on-line by passing an X-ray beam having as a predominant component wavelengths in the range 0.6 to 0.8 Angstrom units through the liquid and detecting the intensity of the transmitted radiation. X-ray wavelengths in this range permit adequate discrimination between attenuation caused by mineral matter and that caused by the liquid, without having very poor transmission. X-ray tubes or radioisotopes can be used as a source.

9 Claims, 3 Drawing Figures

APPARATUS AND METHOD FOR ASSESSING THE CONCENTRATION OF MINERAL MATTER IN COAL-DERIVED LIQUIDS

This invention concerns an apparatus and method for assessing the concentration of mineral matter in coal extracts.

In the production of coal extracts, it is normal to separate as much as possible of the undissolved coal and mineral matter from the extract, to facilitate further processing and to reduce undesirable constituents such as sulphur. Although the present invention will be described hereafter with reference to the extraction of coal using liquid aromatic oil solvents, it is not to be limited thereto and may be used with other methods of extraction such as extracts produced by the contacting of coal with a gaseous solvent above its critical point and in assessing mineral matter in coal-derived liquids generally. To permit the monitoring of the efficiency of the separation process, it is desirable to assess the quantity of mineral matter in the extract after the separation process. A useful method of separation of mineral matter etc. from liquid coal extracts is by filtration, and therefore it is desirable to assess the quantity of mineral matter in the filtrate to ensure that the filtration process is working efficiently. The filtrate downstream of a filter in a coal extraction plant is at a temperature of 200°–300° C. and several bar pressure. It is not believed that there exists an on-stream measurement method for assessment of mineral matter contents in the range from 0 to about 2% in hot liquid coal extracts.

The present applicants, in British Pat. No. 147,725, have described one method of estimating ash by evaporating diluent oil from a sample of coal extract and assessing the reflectance of a freshly-exposed surface. This method takes some 20–30 minutes, which, however, is considerably shorter than a conventional mineral matter analysis as is used for coals.

It has been proposed in a report for the Electric Power Research Institute prepared by West Virginia University, ref. EPRI AF-502 May 1977, to determine, off-line, the amount of solids in suspension in coal-derived liquids using X-ray radiation. A sample of the liquid is introduced into a settling chamber, then time-sequenced X-ray photographs are taken to indicate the position of solids in the settling interface and the height of the liquid surface. Precise measurement of the solids content at the interface can allegedly be determined by densitometry. This procedure would be too slow for effective use in monitoring changes in filter performance.

Radiation transmission or reflectance has been proposed for the assessment of mineral matter in coal itself, for example in run-of-mine coal on a conveyor belt, but such proposals are usually based upon variation from a fixed datum of 25%, 50% etc., and mineral matter levels are very much greater than are encountered in coal liquids and the variations of ash content are also much greater.

The present invention provides a method for the assessment of mineral matter in the range from 0 to about 2% by weight in coal-derived liquids comprising passing an X-ray beam having as a predominant component wavelengths in the range 0.6 to 0.8 Angstrom units through said liquid and detecting the intensity of the transmitted radiation. The method permits the assessment of mineral matter in the very important range of 0–0.2%, and is particularly useful for detecting the reduction of mineral matter content in coal solution filtrate to a predetermined desired level, and thus to detect the point at which the removal of mineral matter, eg by filtration, is effective to give a desired process stream. Therefore, the invention includes a method of controlling filtration in coal extraction technology using the aforesaid method.

The invention also provides an apparatus for use in said method comprising an X-ray source capable of emitting a beam having as a predominant component wavelengths in the range 0.6 to 0.8 Angstrom units and a detector capable of detecting the intensity of the radiation transmitted.

The X-ray source may be an X-ray tube having a target and a filter selected to give the desired beam characteristics or may be a radioisotope source. Of the commercial X-ray tubes, the most available giving radiation in the correct range are those having a molybdenum target, and preferably filtered through zirconium foil. However, other tubes might be constructed with suitable targets including zirconium, yttrium, niobium, ruthenium and rhenium. A suitable radioisotope source is promethium 147 with a zirconium target, but other possible sources are americium 241 or plutonium 238. If the source produces significant amounts of highly penetrating short wavelength radiation, some care is required in matching the characteristics of source and detector to give operation in the desired wavelength range with relatively little detection of radiation which is less selectively absorbed by mineral matter, and this is one reason why proportional counters are preferred. Such X-ray tubes, radioisotopes sources and filters are commercially available. A radioisotope source would permit a more compact apparatus which is more stable; an X-ray tube requires a very stable power supply to avoid fluctuations in output which would lead to inaccuracies in mineral matter assessment.

Success in the application of the present invention lies in the selection of the relatively narrow band of wavelengths comprising between reasonable absorption of the X-ray beam by the coal solution and achieving reasonable discrimination between the attenuation caused by mineral matter and that caused by coal solution itself. Longer wavelengths increase discrimination but the transmission is reduced, and this will be shown in more detail in the Table following. Low transmission may be compensated for by increasing the power of the source, but of course this can have drawbacks in this case of X-ray radiation. The range of wavelenghts given herein is believed to represent the useful range, although there is no sharp cut-off of effectiveness at the ends of the ranges. A wavelength of approximately 0.7 Å appears to be optimum. The radiation used may have one or more peaks in the range 0.6 to 0.8 Å, and the distribution of such peaks within the range is not critical.

Calculations to consider the attenuating effect of the mineral matter and other components of coal solutions on transmitted X-ray radiation of various wavelengths were carried out. Although increasing the wavelength leads to greater attenuation by the mineral matter, the transmitted intensity falls and becomes negligibly small for wavelengths greater than about 0.8 Å because the coal solution itself strongly absorbs such radiation. The fractional intensity transmitted through a 50 mm. thickness of coal solution enclosed between graphite windows 2.5 mm. thick has been calculated for coal solution containing no mineral matter, coal solution containing 10% undissolved ash-free coal, coal solution containing 10% undissolved coal of which 20% is shale, and coal solution containing 10% undissolved coal of which 18% is shale and 2% is pyrite. The following Table gives the calculated values of transmission at different wavelengths and the percentage reduction in transmitted intensity when the coal solution contains undissolved coal with or without mineral matter of two types. The presence of undissolved ash-free coal causes a small percentage reduction whereas mineral matter has a larger effect which depends on the composition. The response of the detector should be calibrated with the particular coal in use, for optimum accuracy.

TABLE

Calculated fractional intensity transmitted through coal solutions containing undissolved solids

| Å | Coal solution | Coal solution containing 10% undissolved | | | % reduction in transmitted intensity for 10% undissolved | | |
|---|---|---|---|---|---|---|---|
| | | ash-free coal | Coal A | Coal B | ash-free coal | Coal A | Coal B |
| 0.20 | 0.345 | 0.337 | 0.333 | 0.331 | 2.3 | 3.5 | 4.1 |
| .417 | .212 | .206 | .194 | .185 | 2.8 | 8.5 | 13 |
| .497 | .149 | .143 | .130 | .120 | 4 | 13 | 20 |
| .631 | .058 | .055 | .045 | .039 | 5 | 22 | 33 |
| .710 | .0268 | .0249 | .0187 | .0152 | 7 | 30 | 43 |
| .880 | .0028 | .0025 | .0014 | .0010 | 11 | 48 | 65 |

Coal A is 80% mineral matter-free coal, with 20% of mineral matter A (21% Al, 22% Si, 55% O, 2% H).

Coal B is 80% mineral matter-free coal, with 20% of mineral matter B (90% mineral matter A, 10% iron pyrites).

The detection of the transmitted X-ray radiation can be done by proprietory equipment such as a Geiger-Muller detector tube. Preferably, however, a conventional proportional counter is used, which can be used in a manner which minimises the effect of unwanted radiations. To permit the invention to be used to assess mineral matter on-line, apparatus is suitably mounted on a pipe carrying filtrate from the filter. As has been stated above, such filtrates are at a temperature of 200°–300° C. and several bar pressure. The assessment of either mineral matter or ash according to the invention may be achieved, for example, by passing the filtrate upwards through a pipe having the apparatus mounted thereon. Since the walls of normal steel pipes strongly absorb X-rays of the wavelengths usable in the invention, and more penetrating X-rays would not be sufficiently sensitive to the changes of mineral matter content in the filtrate, it is essential to use windows in the pipe which permit the passage of X-rays without undue attenuation in the wavelengths used. Graphite is a suitable material, and graphite disc windows are commercially available although they have not been suggested for this use but are used as bursting discs in chemical engineering plant design, although it must be recognised that such bursting discs may not have adequate strength at temperatures above about 180° C. Also suitable as windows, providing that they are engineered to withstand the conditions, are beryllium and boron carbide.

The invention also provides, therefore, an apparatus for the assessment of mineral matter in coal-derived liquids, comprising an X-ray source capable of emitting a beam having as a predominant component wavelengths in the range 0.6 to 0.8 Angstrom units, a detector capable of measuring the intensity of the transmitted radiation after attenuation of the beam by absorption by mineral matter, the source and the detector being mounted in line-of-sight on a pipe or vessel capable of carrying said liquid, said pipe or vessel being provided with windows of a material which does not cause substantial attenuation of the X-ray beam.

The invention will now be described with reference to the accompanying drawings, in which FIG. 1 is a diagrammatic illustration of first embodiment of an apparatus according to the invention.

Figure 2:
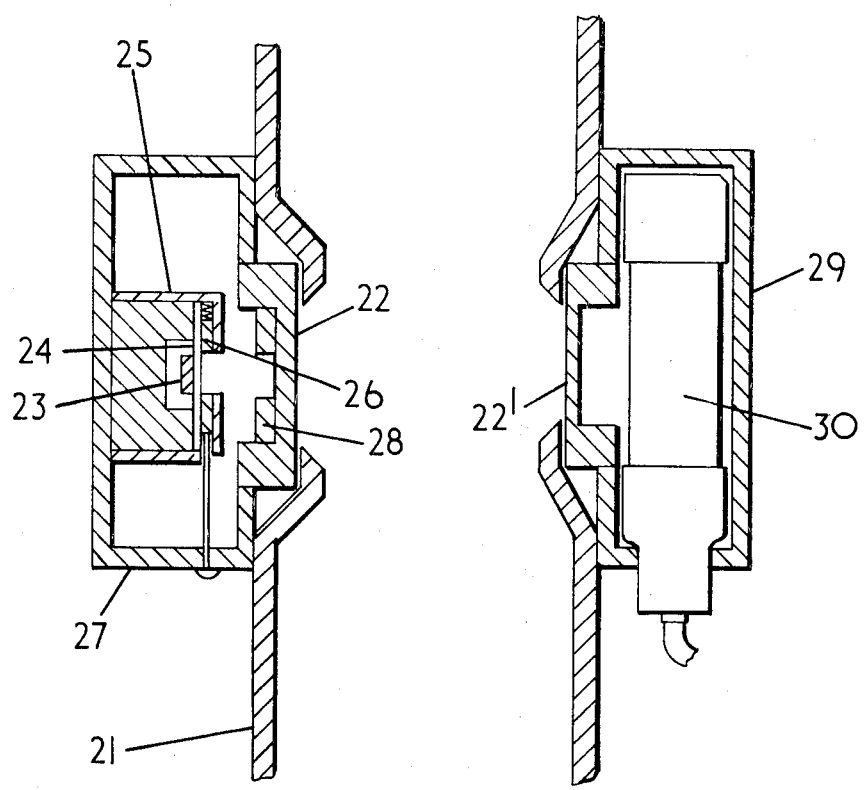
Figure 3:
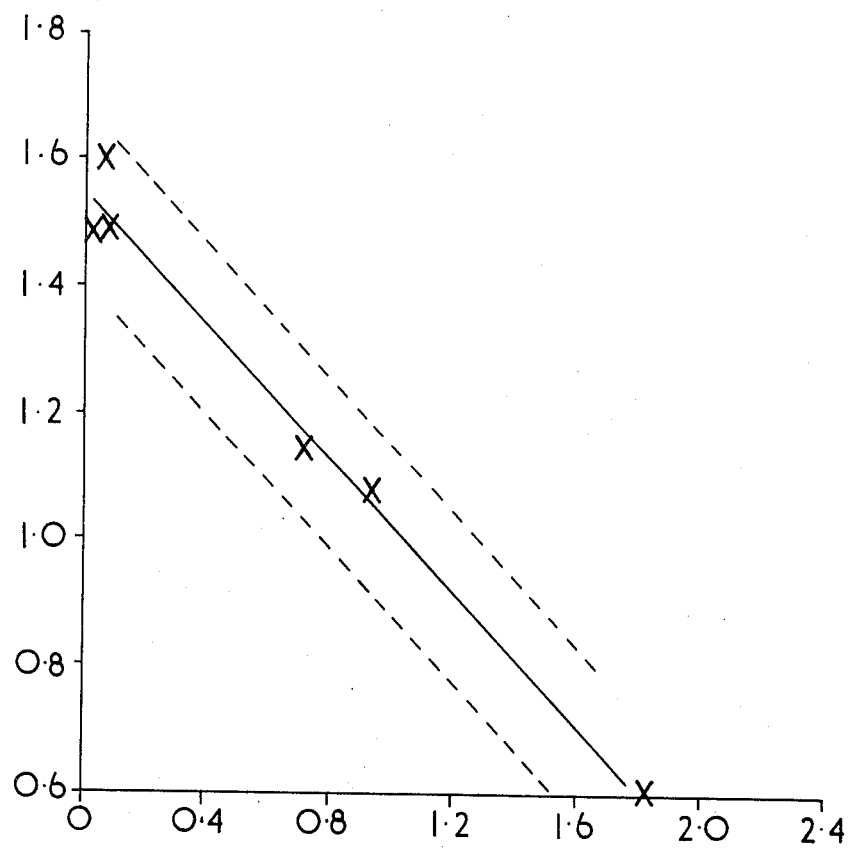

FIG. 2 is a cross-sectional view of a second embodiment of an apparatus according to the invention, and FIG. 3 is a representation of the variation of intensity of X-ray radiation transmitted through samples of coal solution, with measured ash contents.

A sample of coal solution 1, is held in a graphite tube 2, of 2.5 mm wall thickness and 50 mm internal diameter. A commercial X-ray tube 3, having a molybdenum target emits an X-ray beam 4, when in use. The beam 4 passes through a zirconium foil filter 5, of suitable thickness, e.g. 0.108 mm thickness, which absorbs a proportion of the higher energy characteristic and "white" radiations, below about 0.69 Å wavelength, and passes the characteristic Mo Kα peak radiation. The filtered beam is then collimated by passage through an 8 mm diameter aperture in a 2 mm thick lead sheet 6, (producing an irradiated area 12 mm in diameter at the far container wall). The radiation intensity after absorption by the coal solution and container walls is measured over an area of 3 mm diameter formed by an aperture in a further lead sheet 7, using a Geiger-Muller detector tube 8, (Mullard Type MX 122, operated at 940 V) in a lead-lined box 9. Conventional pulse counting techniques are used with sampling periods up to 100 seconds. The counter is represented by A, and its power supply by B.

Operating the X-ray tube at 4 mA tube current, counting for 100 seconds, the variation of intensity with mineral matter content for different samples of coal solutions were measured. FIG. 3 represents the results obtained for several different coal solution/ash contents. The broken lines are the 95% confidence limits. The error indicated is likely to be reduced by the use of a radioisotope source. The y-axis shows intensity in counts/sec and the X-axis shows mineral matter content determined by standard ashing analysis techniques, as a percentage of the solution. An essentially linear relationship is shown, thus permitting a simple assessment of ash or mineral matter content by intensity of radiation after transmission through the coal solution.

The apparatus of FIG. 2 is for use on a pipe carrying coal solution in a coal liquefaction plant. The pipe 21, has mounted on it in conventional manner two graphite windows 22, 22'. An X-ray source 23, (Pm 147/Zr, manufactured by the Radiochemical Centre, Harwell, England) is held in an X-ray source lead shield capsule 25. The capsule 25, has a spring-loaded lead safety shutter 26, which operates to shut off the X-ray emission from the capsule before the capsule can be removed from the lead-shielded container 27, in which it is mounted. A lead disc having an aperture 28, is mounted on window 22 and acts to collimate the beam of X-rays from the source 23. The beam then traverses the coal solution in the pipe and passes through graphite window 22' into a further lead-shielded container 29, in which is mounted a proportional counter 30, which may be, for example, a Harwell type 1,6000 series instrument. The signal from the proportional counter is amplified and passed to a pulse height analyser and sealer/timer to give a direct reading of mineral matter content, the equipment having been previously calibrated according to coal type and solution. The instrumentation can provide an audible or visual warning should the level of mineral matter rise above a preset value and may also provide an automatic control function.

We claim:

1. A method for the assessment of mineral matter in the range 0 to 2% by weight in coal-derived liquids comprising passing an X-ray beam having as a predominant component wavelengths in the range 0.6 to 0.8 Angstrom units through said liquid and detecting the intensity of the transmitted radiation.

2. A method as claimed in claim 1, wherein the X-ray beam has a predominant wavelength of approximately 0.7 Å.

3. An apparatus for the assessment of 0 to 2% of mineral matter in coal-derived liquids comprising:
   a container for said liquid;
   x-ray source means for emitting a beam having as a predominant component wavelengths in the range of 0.6 to 0.8 angstrom units positioned on one side of said container; and
   a detector for detecting the intensity of radiation transmitted through the liquid positioned on an opposite side of the container.

4. An apparatus as claimed in claim 3, wherein the X-ray source is capable of emitting a beam having as a predominant component a wavelength of approximately 0.7 Å.

5. An apparatus as claimed in claim 3, wherein the detector is a proportional counter.

6. An apparatus as claimed in claim 3, wherein the X-ray source is an X-ray tube.

7. An apparatus as claimed in claim 6, wherein the target of the X-ray tube is molybdenum.

8. The apparatus of claim 3, in which the container is a conduit through which the liquid passes.

9. The apparatus of claim 8, in which the conduit is made of steel having windows of x-ray transparent window material on opposite sides of the conduit and mounted in a line of sight relationship.

10. An apparatus for the assessment of 0 to 2% matter in coal-derived liquids comprising a radioisotope having promethium 147/zirconium as an X-ray source capable of emitting a beam having as a predominant component wavelengths in the range 0.6 to 0.8 Angstrom units and a detector capable of detecting the intensity of radiation transmitted through the liquid.

* * * * *